(12) United States Patent
Camara

(10) Patent No.: US 9,671,355 B2
(45) Date of Patent: Jun. 6, 2017

(54) ELECTRON EXCITED X-RAY FLUORESCENCE DEVICE

(71) Applicant: Tribogenics, Inc., Los Angeles, CA (US)

(72) Inventor: Carlos Camara, Los Angeles, CA (US)

(73) Assignee: Tribogenics, Inc., Los Angeles, CA (US)

( * ) Notice: Subject to any disclaimer, the term of this patent is extended or adjusted under 35 U.S.C. 154(b) by 0 days.

(21) Appl. No.: 15/003,571

(22) Filed: Jan. 21, 2016

(65) Prior Publication Data

US 2016/0341679 A1 Nov. 24, 2016

Related U.S. Application Data

(63) Continuation of application No. 13/671,238, filed on Nov. 7, 2012, now Pat. No. 9,244,028.

(51) Int. Cl.
*G01N 23/225* (2006.01)

(52) U.S. Cl.
CPC ... *G01N 23/2252* (2013.01); *G01N 2223/076* (2013.01); *G01N 2223/079* (2013.01); *G01N 2223/309* (2013.01)

(58) Field of Classification Search
USPC ..... 250/310, 306; 378/44, 45, 125, 121, 119
See application file for complete search history.

(56) References Cited

U.S. PATENT DOCUMENTS

| 2,810,077 | A | 10/1957 | Gale |
| 3,612,918 | A | 10/1971 | Willutzki |
| 4,789,802 | A | 12/1988 | Miyake |
| 4,990,813 | A | 2/1991 | Paramo |
| 5,369,275 | A | 11/1994 | Usui et al. |
| 5,665,969 | A | 9/1997 | Beusch |
| 6,233,307 | B1 | 5/2001 | Golenhofen |
| 6,476,406 | B1 | 11/2002 | Struye et al. |
| 6,493,423 | B1 | 12/2002 | Bisschops |
| 6,668,039 | B2 | 12/2003 | Shepard et al. |

(Continued)

FOREIGN PATENT DOCUMENTS

| EP | 0366591 A1 | 5/1990 |
| EP | 1736759 A1 | 12/2006 |

(Continued)

OTHER PUBLICATIONS

Klyuev et al., "The effect of air pressure on the parameters of x-ray emission accompanying adhesive and cohesive breaking solids", Soy. Phys. Tech. Phys., vol. 34, Mar. 1989, pp. 361-364.

(Continued)

*Primary Examiner* — Kiet T Nguyen
(74) *Attorney, Agent, or Firm* — Klein, O'Neill & Singh, LLP

(57) ABSTRACT

A device for providing for electron excited x-ray fluorescence may include means for driving two contacting surfaces against each other in a low fluid pressure environment, such that high energy electrons strike a sample under test and provide for x-ray fluorescence of the sample. The sample under test may be in or on a sample holder, whose position with respect to the contacting surfaces is adjustable. For example, the sample holder may be positionable to be a different distances from the contacting surfaces.

10 Claims, 5 Drawing Sheets

(56) References Cited

U.S. PATENT DOCUMENTS

| | | | |
|---|---|---|---|
| 6,925,151 | B2 | 8/2005 | Harding et al. |
| 7,060,371 | B2 | 6/2006 | Akiyama et al. |
| 7,596,242 | B2 | 9/2009 | Breed et al. |
| 2002/0179864 | A1 | 12/2002 | Fielden et al. |
| 2005/0139771 | A1 | 6/2005 | Imai |
| 2006/0051251 | A1 | 3/2006 | Desrosiers et al. |
| 2007/0022804 | A1 | 2/2007 | Kley |
| 2009/0050847 | A1 | 2/2009 | Xu et al. |
| 2010/0219639 | A1 | 9/2010 | Thompson, Jr. |
| 2010/0290593 | A1 | 11/2010 | Legagneux et al. |
| 2011/0130613 | A1 | 6/2011 | Putterman et al. |
| 2012/0205539 | A1 | 8/2012 | Hlavenka et al. |
| 2013/0336460 | A1* | 12/2013 | Camara .......... H01J 35/02 378/125 |
| 2014/0126692 | A1 | 5/2014 | Camara |

FOREIGN PATENT DOCUMENTS

| | | |
|---|---|---|
| SU | 1149331 A1 | 4/1985 |
| WO | WO 2011/009209 A1 | 1/2011 |
| WO | WO 2012/125492 A2 | 9/2012 |

OTHER PUBLICATIONS

Nakayama et al., "Triboemission of charged particles and photons from solid surfaces during frictional damage", Journal of Physics D. Applied Physics, vol. 25, No. 2, Feb. 14, 1992, pp. 303-308.

Nishitani et al., "STM tip-enhanced photoluminescence from porphyrin film", Surface Science, North-Holland Publishing Co., vol. 601, No. 17, Aug. 23, 2007, pp. 3601-3604.

Ohara et al., "Light emission due to peeling of polymer films from various substrates", Journal of Applied Polymer Science, vol. 14, No. 8, Aug. 1, 1970, pp. 2079-2095.

Kluev et al., "Gas—Discharge Phenomena, Accompanying the Process of Breaking an Adhesion Contact in Vacuum", IAS Annual Meeting, Oct. 2-6, 1977, Los Angeles, CA, USA, Jan. 1, 1997, pp. 596-598.

International Search Report on related PCT Application No. PCT/US2013/068997 from International Searching Authority (KIPO) dated Feb. 12, 2014.

Written Opinion on related PCT Application No. PCT/US2013/068997 from International Searching Authority (KIPO) dated Feb. 12, 2014.

Examination Report on European Application No. 09711141.3 from the European Patent Office (EPO) dated Oct. 9, 2014.

Fazal et al., Design, fabrication and characterization of a novel gas microvalve using micro—and fine-machining, May 2006, J. Micromech. Microeng. vol. 16, pp. 1207-1209.

U.S. Appl. No. 13/671,238, filed Nov. 7, 2012, Carlos Camara, Office Action Aug. 27, 2014, Notice of Allowance Apr. 21, 2015, Sep. 21, 2015.

Extended European Search Report on European Application No. 13853404.5 from the European Patent Office (EPO) dated May 27, 2016.

Examination Report on European Application No. 13853404.5 from the European Patent Office (EPO) dated Mar. 24, 2017.

\* cited by examiner

ELECTRON EXCITED X-RAY FLUORESCENCE DEVICE

CROSS-REFERENCE TO RELATED APPLICATION

The present application is a continuation of U.S patent application Ser. No. 13/671,238, filed Nov. 7, 2012, the disclosure of which is incorporated by reference herein.

BACKGROUND OF THE INVENTION

The present invention relates generally to generation of high-energy electrons, and more particularly to electron excited x-ray fluorescence (EXRF).

High-energy electrons may be used for medical or other material excitation applications such as etching or probing.

Other than through natural phenomena, high-energy electrons are generally generated by high voltage accelerators that require high voltage power supplies. When electrons of a sufficient energy strike a target or sample, they can dislodge an inner shell electron creating a vacancy. When this vacancy is filled by the capture of outer shell electrons, an x-ray with characteristic energy is emitted. This process may be referred to as electron excited x-ray fluorescence (EXRF). Conventional x-ray fluorescence is carried out by the excitation of inner shell electrons by x-ray irradiation. This process requires the use of an x-ray source. X-ray generators are inherently inefficient because the conversion of high energy electricity to x-rays takes place through collisions, only a small fraction of which have sufficient energy to result in x-ray radiation.

BRIEF SUMMARY OF THE INVENTION

Aspects of the invention provide for electron excited x-ray generation.

One aspect of the invention provides an electron excitation x-ray fluorescence (EXRF) device, comprising: a chamber maintainable at a desired fluid pressure; a vacuum pump coupled to the chamber, whereby the vacuum pump may at least partially evacuate the chamber; a membrane sufficiently transparent to x-rays within the chamber; a gapped rotor drivable to provide time varying contact with areas of a first surface of the membrane; a sample holder including a sample holding area for holding samples within the chamber during operation; and a sealable port in the chamber to provide access to the sample holding area.

Another aspect of the invention provides an electron excitation x-ray fluorescence (EXRF) device, comprising: a chamber; a vacuum pump coupled to the chamber to maintain the chamber at a desired fluid pressure; a first surface and a second surface in at least partial contact with one another within the chamber, at least one of the first surface and the second surface being drivable so as to vary the portion of area of at least one of the first surface or the second surface in contact with the other surface; a sample holder within the chamber, the sample holder positioned in the chamber so as to have an at least partially clear line of sight to an area of the first surface as areas of the first surface exit contact with the second surface; an electron source such as a filament of a Tungsten alloy, placed in the volume between the first surface and the sample holder; and an x-ray detector positioned so as to have an at least partially clear line of sight to x-rays coming from the sample holder region.

These and other aspects of the invention are more fully comprehended upon review of this disclosure.

BRIEF DESCRIPTION OF THE FIGURES

FIG. 2 illustrates aspects of operation of a device such as the device of FIG. 1;

DETAILED DESCRIPTION

Figure 1:
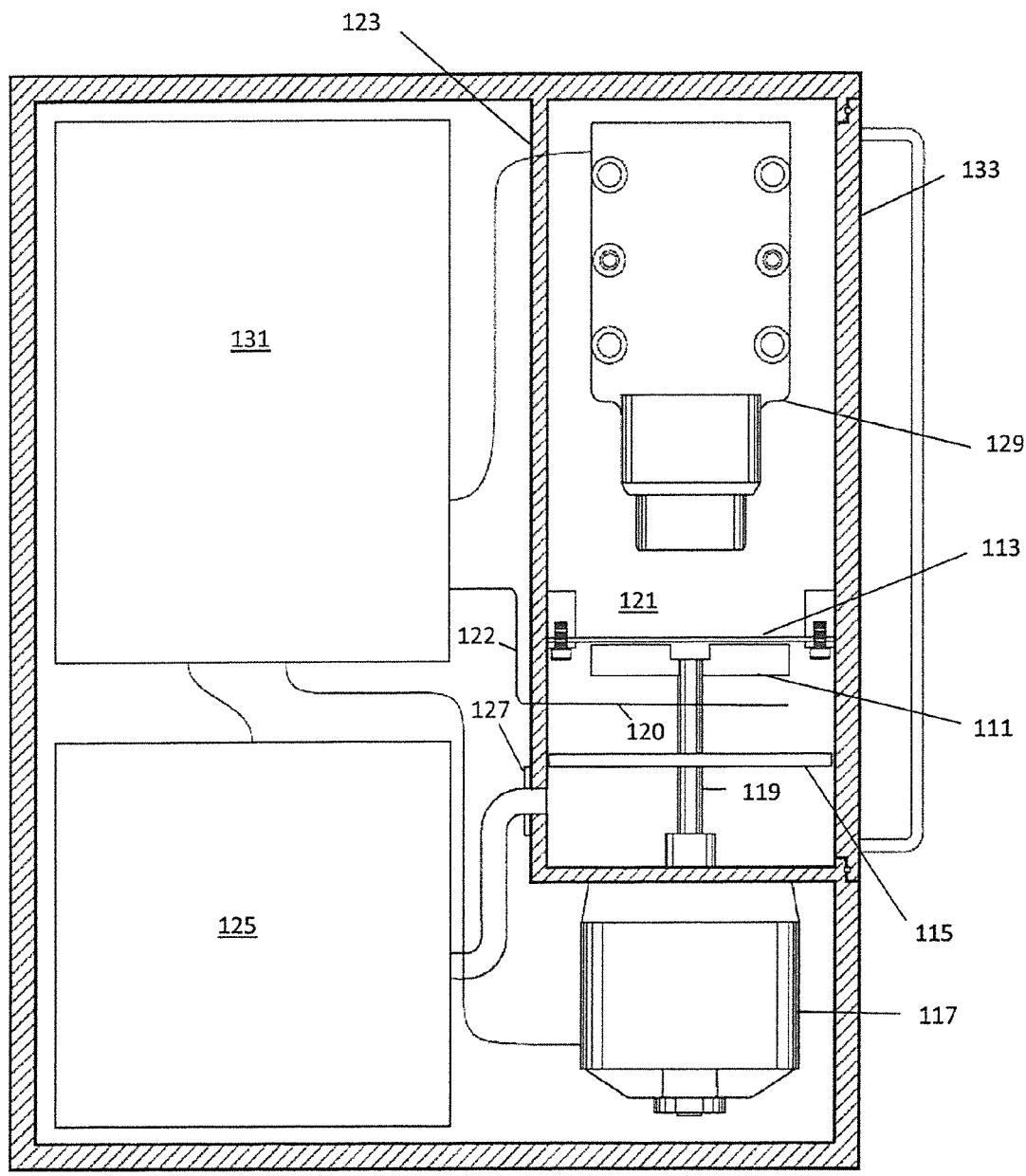
FIG. 1 illustrates a cutaway view of a benchtop electron excited x-ray fluorescence device in accordance with aspects of the invention.

FIG. 1 illustrates a cutaway view of an EXRF device in accordance with aspects of the invention. The EXRF device includes a rotor 111 positioned to be in moveable contact with a membrane 113 during rotation of the rotor. The rotor may be mounted on a shaft 119, which is rotated by a motor 117. In various embodiments the motor may be replaced with various other drive mechanisms, for example a magnetic drive assembly or the like. The rotor and the membrane are in a chamber 121 bounded by walls 123. The membrane is generally of an electrically insulating material, although in various embodiments the membrane may include metal or metallic components, and in various embodiments the membrane is or forms a dielectric material. In various embodiments the membrane is at least partially transparent to x-rays, and in some embodiments the membrane is of a polyimide film such as Kapton or is of ethylene tetrafluoroethylene (ETFE). The chamber is maintained at a desired fluid pressure by a vacuum pump 125 coupled to the chamber by a port 127. The desired fluid pressure is generally less than 100 mTorr, or in various embodiments 50 mTorr, 1 mTorr, or 0.001 mTorr. Also within the chamber, rearward of the rotor, with the membrane considered to be forward of the rotor, is a sample tray 115. Access to the sample tray may be conveniently provided by way of a sealable door 133 in a wall of the chamber. In some embodiments position of the sample tray is adjustable relative to position of the membrane.

Moving contact of portions of the rotor, which may be of metallic portions of the rotor, and the membrane results in portions of the rotor being in time-varying contact with varying areas of the surface of the membrane. The moving contact may be, in various embodiments, frictional contact, sliding contact, or rolling contact. In such circumstances, the varying contact results in relative electrical charging between the contacting materials, where the materials are chosen so that the membrane becomes negatively charged. This charge imbalance sets an electric field with a potential proportional to the magnitude of the surface charge density. Electrons, and/or in some embodiments ions, within this field will accelerate away from the surface with the same sign of charge, towards surfaces of opposite or lesser charge. The energy attainable by the charged particles is generally controlled by their initial position and the distance between the charged surfaces. Some of the accelerated electrons may strike portions of the rotor and some of the electrons may also strike a sample in the sample tray. A sufficient charge density will accelerate electrons such that their collisions will result in the emission of x-rays.

In some (but not all) embodiments an electron source 120 is provided in the vicinity of the membrane. As illustrated in the embodiment of FIG. 1, the electron source is an exposed metallic filament, for example of a tungsten alloy, in some embodiments. As illustrated in the embodiment of FIG. 1, the filament is coupled by a wire to control electronics 131, which provides current to the filament, and for example controls the flow of electrons. The control electronics may provide, for example a 2 Amp current to the filament, for example using a 3 Volt voltage supply. The position of the filament can be chosen to control the location of the source of electrons. In some embodiments the filament could be at a fixed position. In other embodiments the filament could be mounted on a controllable stage, for example to vary relative position of the filament with respect to the contact surfaces or the sample holder.

The electrons striking the sample cause x-ray fluorescence of the sample, with the sample generated x-rays having characteristics dependent on elemental composition of the sample. The x-rays pass to a detector 129, which in the embodiment of FIG. 1 is also within the chamber. The detector is coupled to control electronics 131. The control electronics may process signals from the detector, command operation of the vacuum pump and the motor, and provide signals to external memory and/or displays.

In some embodiments the membrane extends from a spool (not shown), with material of the membrane also wrapped on the spool. As membrane material become worn, or as desired, additional material may be unwound from the spool to provide a fresh contact surface for blades of the rotor. In some embodiments the spool is within the chamber 121.

In some embodiments the x-ray detector is positioned in other positions, for example to the side of the membrane and sample holder, as viewed in FIG. 1. In such embodiments the vacuum pump and control electronics may be appropriately repositioned to make room for the x-ray detector, and the shape of the chamber 121 may be adjusted for such a configuration or the x-ray detector may have an exposure to the chamber by way of a window, for example a beryllium window. In some embodiments two x-ray detectors may be used, with for example one positioned as shown in FIG. 1 and another positioned to the side of the membrane and sample holder.

In some embodiments the sample holder may be transparent or substantially transparent to x-rays. In some embodiments the sample holder may be opaque to x-rays. In some embodiments the sample holder may contain certain predetermined elements. The use of predetermined elements in the sample holder may be beneficial in that operation of the device, without samples, would be expected to provide x-ray emissions characteristic of the predetermined elements, allowing for ease of calibration of the device. For example, prior to testing of samples, the device may be operated with an empty sample holder to obtain a baseline response of the device. In various embodiments the baseline response may thereafter be subtracted from operational responses obtained during testing of materials.

FIG. 2 illustrates conceptual operation of a device such as the device of FIG. 1. In operation, a motor 211 rotates a drive shaft 213. A rotor 215 is mounted to the drive shaft, with blades of the rotor extending away from an axis of rotation of the drive shaft. The blades of the rotor are in contact with a membrane 217, with the blades sweeping across areas of the membrane. As the blades clear any particular area of the membrane, the negative surface charge in the membrane is exposed. Free or weakly bound electrons in the vicinity of the membrane will accelerate away from the membrane 219. An electron source such as a Tungsten alloy, can be used to generate free electrons in the vicinity of the membrane, for example as discussed with respect to FIG. 1. At least some of the electrons travel away from the membrane, past the rotor, and strike a sample in a sample tray 221. This results in electron excited x-ray fluorescence of the sample, with x-rays 223 impinging on a detector 225.

Figure 3:
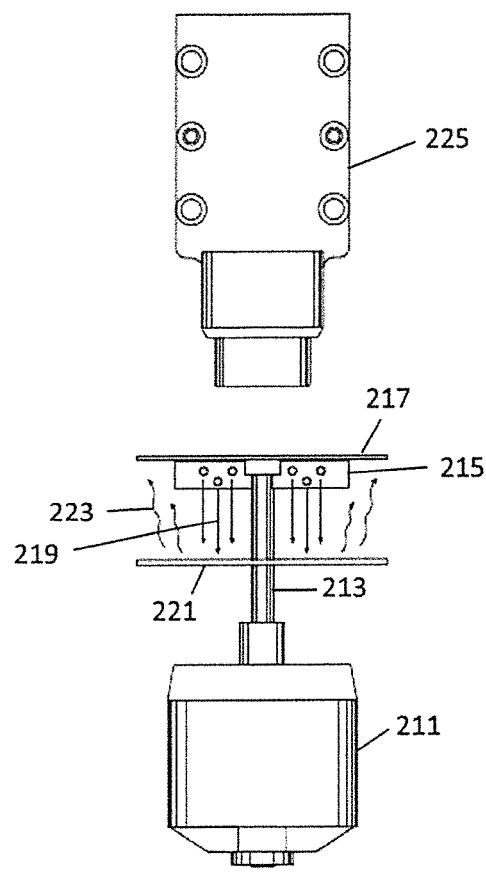
FIG. 3 illustrates an example rotor useful in aspects of the invention.
Figure 4:
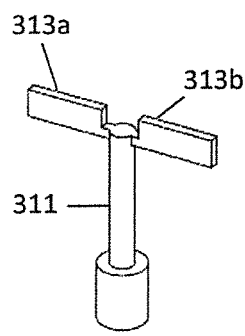
FIG. 4 illustrates an example further rotor useful in aspects of the invention.
Figure 5:
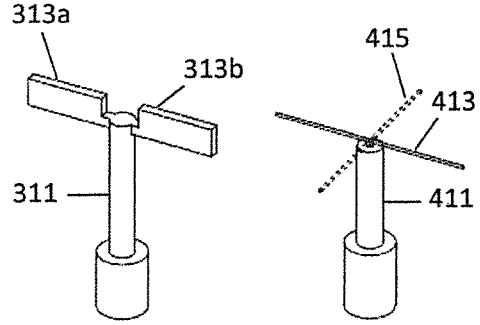
FIG. 5 illustrates an example still further rotor useful in aspects of the invention.
Figure 7:
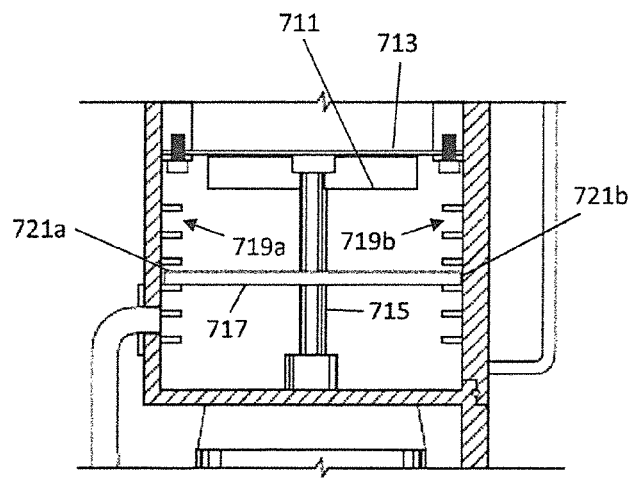
FIG. 7 illustrates a further sample tray adjustment mechanism in accordance with aspects of the invention.

FIGS. 3-5 illustrate example rotors mounted on drive shafts in accordance with aspects of the invention. In FIG. 7, a pair of wings 313a,b extend away from each other about a distal end of a drive shaft 311. In FIG. 4, a vane 413 extends from a distal end of a drive shaft 411, with an optional additional vane 415 also possible. In FIG. 5 a pair of rollers 513a,b are rollably coupled to a drive shaft 511 by a wire 515 or other mount. In operation the rollers roll over areas of a membrane or other contact material.

Figure 6:
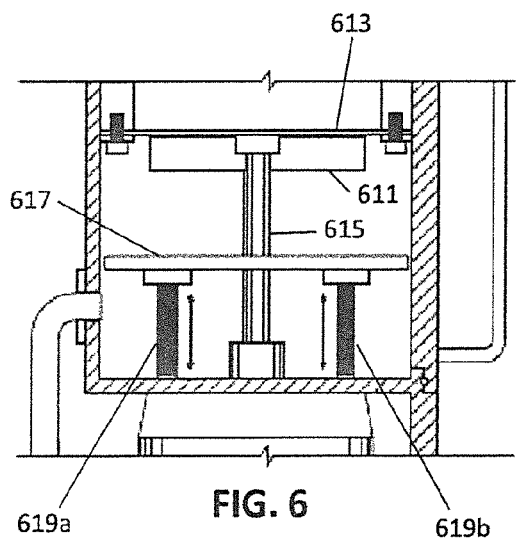
FIG. 6 illustrates a sample tray adjustment mechanism in accordance with aspects of the invention.

FIG. 6 illustrates a portion of a device such as the device of FIG. 1 with an adjustment mechanism for adjusting position of a sample tray 617 with respect to a membrane 613. Generally the adjustment mechanism may be a height adjustment mechanism. In FIG. 6, blades 611 of a rotor coupled to a drive shaft 615 brush against the membrane during rotation of the drive shaft. Electrons generated by this operation strike a sample on the sample tray, resulting in electron excited x-ray fluorescence of the sample.

Position of the sample tray relative to the membrane is provided by adjustment rods 619a-b, which may be raised or lowered with respect to a base of a chamber including the sample tray and the membrane. In some embodiments the adjustment rods are telescopic assemblies, which may be extended or retracted to provide for different distances between the sample tray and the membrane.

FIG. 7 illustrates a further example of a device providing for adjustable position of a sample tray with respect to a membrane. As shown in FIG. 7, opposing walls of the chamber include a plurality of pairs of slots, for example a first pair of slots 719a,b and a used pair of slots 721a,b. A sample tray 717 is placed in the used pair of slots, although the sample tray may instead be placed in any of the other pairs of slots. As the pairs of slots define positions at varying distances from the membrane, the slots provide for adjustable positioning of the sample tray with respect to the membrane.

Figure 8:
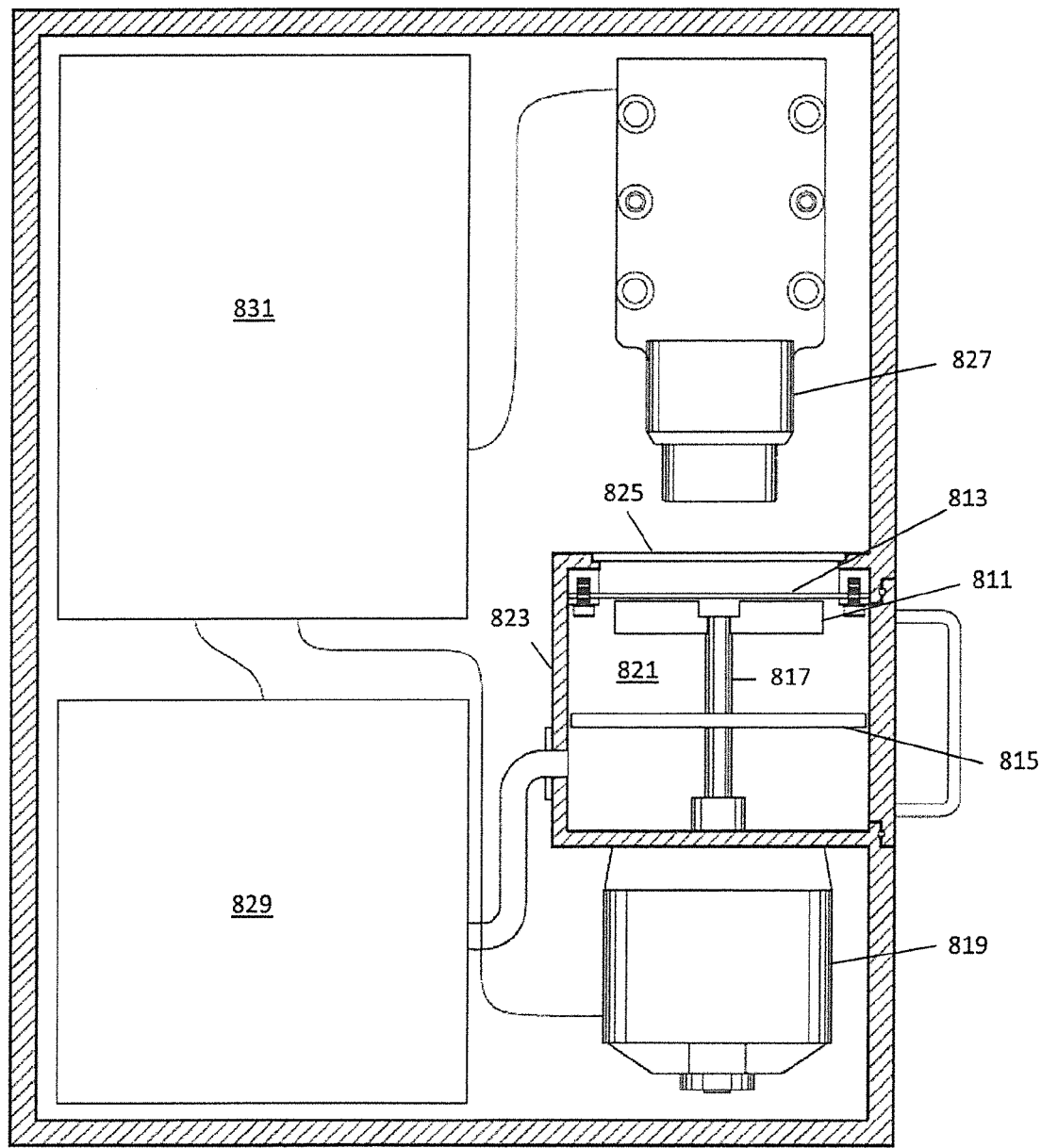
FIG. 8 illustrates a cutaway view of a further benchtop electron excited x-ray fluorescence device in accordance with aspects of the invention.

FIG. 8 illustrates a cutaway view of a further EXRF device in accordance with aspects of the invention. The embodiment of FIG. 8 is similar to the embodiment of FIG. 1. As with the embodiment of FIG. 1, The EXRF device includes a rotor 111 positioned to be in moveable contact with a membrane 113 during rotation of the rotor. The rotor may be mounted on a shaft 119, which is rotated by a motor 117. The rotor and the membrane are in a chamber 121 bounded by walls 123. The chamber is maintained at a desired fluid pressure by a vacuum pump 125 coupled to the chamber by a port 127. The desired fluid pressure is generally less than 0.001 Torr. Also within the chamber, rearward of the rotor, with the membrane considered to be forward of the rotor, is a sample tray 115. Access to the sample tray may be conveniently provided by way of a sealable door 133 in a wall of the chamber. In some embodiments position of the sample tray is adjustable relative to position of the membrane.

During operation, x-ray emissions from samples in the sample tray pass through the bezel 825 to impinge on the detector 827. The detector provides signals to control electronics 831.

Figures 9, 10:
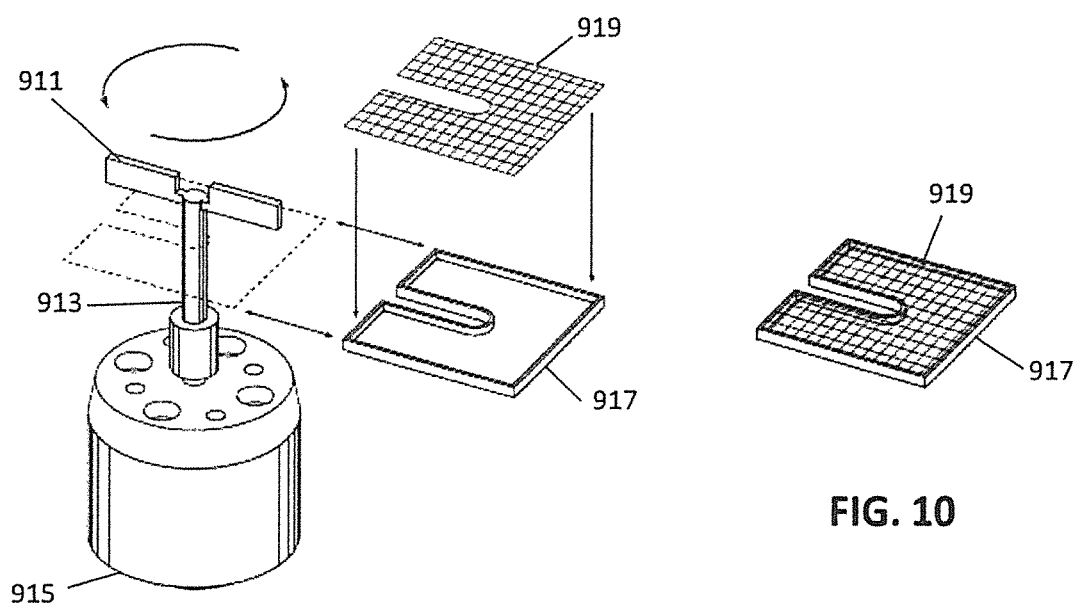
FIG. 9 illustrates an exploded view of portions of a device with a voltage potential mesh.
FIG. 10 illustrates a sample tray with a voltage potential mesh.

FIG. 9 illustrates an exploded view of portions of an EXRF device in accordance with aspects of the invention. In FIG. 9, a bladed rotor 911 is mounted to a motor shaft 913 driveable by a motor 915. A sample tray 917, having a slot for insertion about the motor shaft, is positionable between the motor and the rotor. A wire mesh 919 is positionable over a top of the sample tray, for example as may be seen in FIG. 10. The wire mesh may, in some embodiments and in some applications, serve to restrain or retain samples in the sample tray.

In some embodiments, the wire mesh is coupled to a voltage source, with the wire mesh maintained at some desired potential. The desired potential may be sufficiently positive to attract free electrons, for example generated in the embodiments of FIG. 1 or 8, towards the sample tray. In some embodiments the desired potential is sufficiently positive to attract electrons towards the sample tray, but not so positive that the wire mesh is so attractive to electrons that the sample receives fewer electrons than the sample would receive if the wire mesh were not present, or was not maintained at any particular potential.

Although the invention has been discussed with respect to various embodiments, it should be recognized that the invention comprises the novel and non-obvious claims supported by this disclosure.

What is claimed is:

1. An electron excitation x-ray fluorescence (EXRF) device, comprising:
   a chamber maintainable at a desired fluid pressure;
   a vacuum pump coupled to the chamber, whereby the vacuum pump may at least partially evacuate the chamber;
   a membrane of a dielectric material within the chamber;
   a gapped rotor drivable to provide time varying contact with areas of a first surface of the membrane;
   a sample holder including a sample holding area for holding samples within the chamber during operation; and
   a sealable port in the chamber to provide access to the sample holding area.

2. The device of claim 1, wherein the sealable port comprises a door in a wall of the chamber.

3. The device of claim 1, wherein the sealable port is a slot in a wall of the chamber.

4. The device of claim 3, wherein position of the sample holder is adjustable with respect to position of the membrane.

5. The device of claim 3, further comprising means for adjusting position of the sample holding area with respect to the membrane.

6. The device of claim 1, wherein a distance between the membrane and the sample holding area is adjustable.

7. The device of claim 1, wherein the sample holder is substantially opaque to x-rays.

8. The device of claim 1, wherein the sample holder is substantially transparent to x-rays.

9. The device of claim 1, further comprising a mesh over a sample tray.

10. The device of claim 9, wherein the mesh is maintained at a predefined electrical potential.

* * * * *